United States Patent [19]

Swedberg

[11] Patent Number: 5,085,756
[45] Date of Patent: Feb. 4, 1992

[54] COLUMN SEPARATION SYSTEM FOR ELECTROPHORESIS WITH SAMPLE PRETREATMENT

[75] Inventor: Sally A. Swedberg, Santa Cruz, Calif.

[73] Assignee: Hewlett-Packard Company, Palo Alto, Calif.

[21] Appl. No.: 570,480

[22] Filed: Aug. 21, 1990

[51] Int. Cl.⁵ .......................................... G01N 27/26
[52] U.S. Cl. ........................... 204/299 R; 204/182.8; 204/183.3; 204/301
[58] Field of Search ............. 204/182.8, 183.3, 299 R, 204/301

[56] References Cited

U.S. PATENT DOCUMENTS

| | | | |
|---|---|---|---|
| 4,305,799 | 12/1981 | Schwarz et al. | 204/182.9 |
| 4,675,300 | 6/1987 | Zare et al. | 204/180.1 |
| 4,708,782 | 11/1987 | Andresen et al. | 204/299 R |
| 4,865,706 | 9/1989 | Karger et al. | 204/182.8 |

OTHER PUBLICATIONS

Jorgenson and Lukacs, "High-Resolution Separations Based on Electrophoresis and Electroosmosis", *J. Chromatog.*, 218 (1981), pp. 209–216.
Jorgenson and Lukacs, "Zone Electrophoresis in Open-Tubular Glass Capillaries", *Anal. Chem.*, 53 (1981) pp. 1298–1302.
Jorgenson and Lukacs, "Capillary Zone Electrophoresis", *Science*, 222 (1983), 266–272.
Hjerten, "High-Performance Electrophoresis Elimination of Electroendosmosis and Solute Adsorption", *J. Chromatogr.*, 347 (1985), 191–198.
Bruin et al., "Performance of Carbonhydrate-Modified Fused-Silica Capillaries for the Separation of Proteins by Zone Electrophoresis", *J. Chromatogr.*, 480 (1989), 339–349.
Bruin et al. "Capillary Zone Electrophoretic Separations of Proteins in Polyethylene Glycol-Modified Capillaries", *J. Chromatogr.*, 471 (1989), 429–436.
Swedberg, "Characterization of Protein Behavior in High-Performance Capillary Electrophoresis Using a Novel Capillary System", *Anal. Biochem.*, 185 (1990), 51–56.
Lauer and McManigill, "Capillary Zone Electrophoresis of Proteins in Untreated Fused Silica Tubing", *Anal. Chem.*, 58 (1986), 166–170.
Cohen, "High-Performance Capillary Electrophoresis Separation of Bases, Nucleosides, and Oligonucleotides: Retention Manipulation via Micellar Solutions and Metal Additives", *Anal. Chem.*, 59 (1987) 1021–1027.
Roach et al., "Determination of Methotrexate and its Major Metabolite, 7-Hydroxymethotrexate, Using Capillary Zone Electrophoresis and Laser-Induced Fluorescence Detection", *J. Chrom.*, 426 (1988) 129–140.
McCormick, "Capillary Zone Electrophoretic Separation of Peptides and Proteins Using Low pH Buffers in Modified Silica Capillaries", *Anal. Chem.*, 60 (1988), 2322–2328.

*Primary Examiner*—John Niebling
*Assistant Examiner*—David G. Ryser

[57] ABSTRACT

Capillary tubes useful for performing capillary zone electrophoresis separation techniques are modified to provide sample pre-treatment in situ. In one preferred embodiment, a polyacrylamide stacking gel is formed in a capillary tube and separated from the free zone of the tube by a polystyrene frit. The modified capillary permits effective filtration of macromolecules from analysis or their retardation to allow for sequential analysis.

7 Claims, 1 Drawing Sheet

COLUMN SEPARATION SYSTEM FOR ELECTROPHORESIS WITH SAMPLE PRETREATMENT

FIELD OF THE INVENTION

The present invention generally relates to capillary zone electrophoresis and more particularly to capillary tubes useful for electrophoretic separations that are modified to provide in situ sample pretreatment.

BACKGROUND OF THE INVENTION

Capillary zone electrophoresis ("CZE") in small bore capillaries was first demonstrated by Jorgenson and Lukacs, and has proven useful as an efficient method for the separation of certain small solutes. *J. Chromatog.*, 218 (1981), 209; *Anal. Chem.*, 53 (1981), 1298. In CZE, an electric field is applied between the two ends of a capillary tube into which an electrolyte containing the solutes is introduced. The electric field causes the electrolyte to flow through the tube. Some solutes will have higher electrokinetic mobilities than other solutes so that the sample components are resolved into zones in the capillary tube during the flow of the electrolytes through the capillary.

Attractive factors for CZE include the small sample sizes, high resolution, automation, and the potential for quantification and recovery of biologically active samples. For example, U.S. Pat. No. 4,675,300, inventors Zare et al., describes theories and equipment for electrokinetic separation processes employing a laser-excited fluorescence detector. The system described by Zare et al. includes a fused silica capillary with a 75μ inner diameter. CZE has been increasingly used in the analysis of a variety of substances, such as amino acids, proteins, nucleotides, nucleosides and drugs.

Jorgenson and Lukacs reported problems associated with the separation of proteins. It was found that most of proteins exhibit significant adsorption to the surface of both fused silica and borosilicate glass capillaries. They concluded that adsorption affects electropherograms in two undesirable ways. First, it leads to broad asymmetric "tailed" zones. Second, adsorbed proteins modified the capillary surface, usually decreasing electroosmotic flow significantly which leads to unpredictable migration for all sample zones upon repeated injection. Jorgenson and Lukacs, *Science*, 222 (1983), 266.

Lauer and McManigill, *Anal. Chem.*, 58 (1986), 166, have reported that the Coulombic repulsion between proteins and the capillary wall of silica capillaries can overcome adsorption tendencies of the proteins with the capillary wall. They demonstrated separations of model proteins (ranging in molecular weight from 13,000 to 77,000) by varying the solution pH relative to the isoelectric point (pI) of the proteins to change their net charge. Several other approaches have employed to eliminate the wall absorption of proteins: applying very low pH values so that the silanol groups are largely protonated and result in a small electrical charge on the wall; and chemical modification of the wall with a neutral, hydrophilic moiety in order shield the silanol groups. See Swedberg, "Characterization of Protein Behavior in High-Performance Capillary Electrophoresis Using a Novel Capillary System", *Anal. Biochem.*, 185 (1990) 51; Bruin et al., "Performance of Carbohydrate-Modified Fused-Silica Capillaries for the Separation of Proteins by Zone Electrophoresis", *J. Chromatogr.*, 480 (1989), 339; Bruin, et al., "Capillary Zone Electrophoretic Separations of proteins in Polyethylene Glycol-Modified Capillaries", *J. Chromatogr.*, 471 (1989), 429; McCormick, "Capillary Zone Electrophoretic Separation of Peptides and Proteins Using Low pH Buffers in Modified Silica Capillaries", *Anal. Chem.*, 60 (1988), 2322; and Hjerten, "High-Performance Electrophoresis Elimination of Electroendosmosis and Solute Adsorption", *J. Chromatogr.*, 347 (1985), 191.

Increasing the selectivity control of capillary electrophoresis has been achieved through the use of anionic micelles from sodium dodecyl sulfate (SDS). This approach has been used to separate bases, nucleosides and nucleotides in a buffer solution with a pH of 7. Since the bases and nucleosides are uncharged at the pH of operation, separation is a result of differential partition within the interior of the micelle; the more hydrophobic the species, the larger the partition coefficient and the larger the retention. Oligo-nucleotides are negatively charged and can be separated without SDS micelles; however, the time window is narrow and separation of complex mixtures is limited. The combination of low concentrations of divalent metals and SDS micelles leads to a significant enhancement of the time window and good separation of oligonucleotides. The metal ion is electrostatically attracted to the surface of the micelle and differential metal complexation of the oligonucleotides with the surface of micelles leads to separation of complex mixtures. See Cohen, *Anal. Chem.*, 59 (1987), 1021.

Traditional analysis of species in a complex matrix requires pretreatment steps such as extraction or precipitation to partially clean the sample to rid it of interferants. See Roach et al., *J. Chromatogr.*, 426 (1988), 129. However, pretreatment increases analysis time and increases the probability of contamination and of the inadvertent elimination of solutes from analysis.

SUMMARY OF THE INVENTION

It is an object of the present invention to provide capillary tubes with a polymer gel filter that are useful for electrophoretic separations of solutes in which the filter excludes interferants from the solutes prior to analysis.

It is another object of the present invention to provide capillary tubes with a polymer gel filter whose polymeric cross-linkage can be adjusted so that the flow of macromolecules is retarded to permit sequential analysis, that is, the analysis of small solutes followed by the analysis of large ones.

It is a further object of the present invention to provide capillary tubes useful for rapid electrophoretic separations based, at least in part, on charge differences and with substantially quantitative results. Other objects and advantages of the invention will be apparent to those skilled in the art to which the invention pertains.

In one aspect of the present invention, a capillary tube useful for electrophoretic separations of solutes comprises a polyacrylamide gel filter disposed near the end of the tube from which samples are injected. The length of the filter, the gel concentration and the degree of its cross-linkage determine the sieving properties of the filter. The higher the gel concentration and degree of cross-linkage, the lower the permeability of the filter. Thus, the filter may be employed to totally exclude interferants; alternatively, the filter can be used only to retard certain solutes, thereby permitting sequential analysis of small solutes before analysis of macromolecules. In this embodiment, the free zone of the capillary is separated from the gel filter by a polystyrene frit.

Capillary tubes of the invention are preferably prepared by first melting polystyrene in a capillary tube and allowing the melt to cool, thereby forming a porous frit. Next, a silylating reagent, such as 3-acryloxypropyl methoxysilane, is coated onto the inner tubing on one side of the frit. The capillary tube is then flushed with helium to cure the silylating reagent onto the walls of the capillary tube. Finally, polyacrylamide is placed into the same side of the tube coated with silylating reagent and thereafter the polymer is allowed to gel.

DETAILED DESCRIPTION OF THE PREFERRED EMBODIMENTS

Small bore capillary tubes useful in capillary zone electrophoresis ("CZE") usually have bore diameters less than about 500 microns, often less than 200 microns. Typical bore sizes for use with the present invention are from about 75 microns to about 500 microns, more usually about 75 microns to about 200 microns. In the present invention, a capillary tube is modified to define a first and second portion, with a small diameter bore through the second portion. The first portion includes means for sieving molecules by molecular weight, while the second portion is of a construction sufficient to permit separation of molecules by electric charge (such as conventionally is performed in CZE). The first and second portions are contiguous so that fluid with sample flows readily from the first portion to the second portion during separations.

As described further herein, the invention provides in situ pretreatment of samples to be analyzed, thereby obviating the need for cumbersome off-line pretreatment that often times increases analytical error. Moreover, aside from filtering interferants from samples, the inventive device also can be employed to retard the flow of large macromolecules, thereby providing means for introducing solutes into the second portion of the device for analysis on a sequential basis, that is, with smaller solutes being introduced (and analyzed) first, followed by larger ones.

In a preferred embodiment, a polyacrylamide gel plug in the front end of an open capillary functions as the sieving means of the first portion and acts as a filter to exclude or retard macromolecules of a certain (selected) molecular weight range. The large macromolecules are retarded in the gel, allowing the smaller solutes to penetrate the "free zone" of the second portion and hence be analyzed preferentially. It is contemplated that the degree of cross-linking of the gel in the first portion can be modified so that large molecules such as proteins can be analyzed after the small solutes. However, the degree of cross-linkage can be increased so that during the course of analysis macromolecules never entirely penetrate the gel. In this regard, the gel acts as a molecular weight filter in situ.

Figure 1:
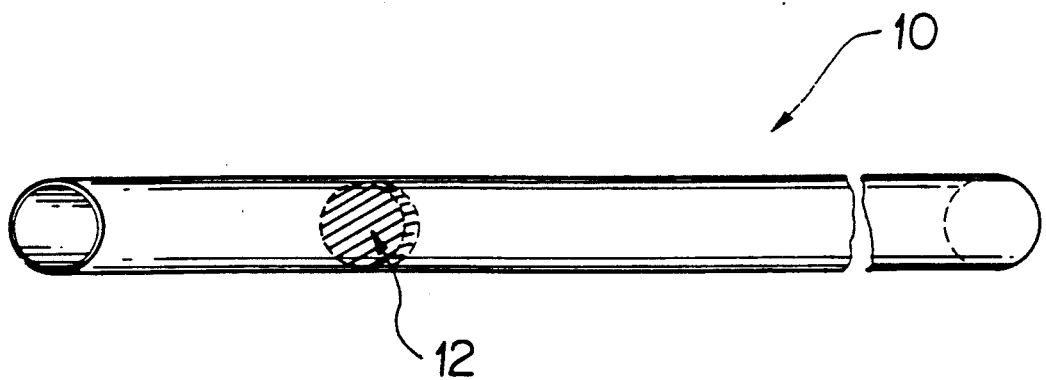
FIG. 1 is a perspective view of a capillary tube partially coated with a silylating reagent and containing a polystryrene frit.
Figure 2:
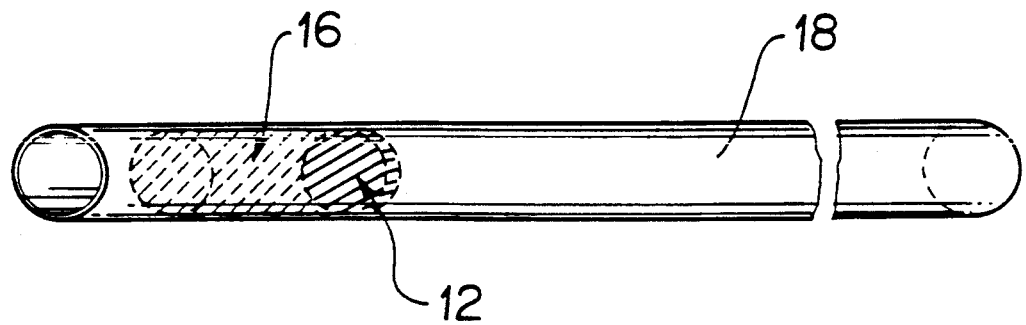
FIG. 2 is a perspective view of one embodiment of the modified capillary tube.

As shown in FIG. 1, preparation of the modified capillary tube in accordance with the present invention preferably begins with depositing some polystyrene in capillary tube 10. (Commercially available polystyrene, MW 2030, in powder form was used, although different molecular weight polystyrene polymers could be used.) Normally, the polystyrene is positioned approximately 2 cm from one end of the tube. Thereafter, the polystyrene is heated and the melt allowed to cool to produce a frit 12 which effectively divides the capillary into two sections (that is, precursors of the second and first portions). The resulting porous polystyrene frit was well-annealed in place; that is, solutions easily passed through it at high flow rates without adversely affecting the structured integrity of the frit. Silylating reagent, such as 3-acryloxypropylmethoxysilane, is coated onto the inner surface of one section of the capillary tube 10. The silylating reagent promotes adhesion of the polymer gel onto the inner capillary surfaces. Helium is thereafter passed through the capillary tube to cure the silylating agent onto the walls of the capillary tube. Finally, gelforming materials such as polyacrylamide are placed into the section of the capillary tube containing the cured silylating reagent. The tube is ready for use once the polyacrylamide gels. The modified capillary as shown in FIG. 2 has a gel stack 16, a polystyrene frit 12, and a free zone 18.

In another embodiment, a silica plug is employed instead of a polystyrene frit. In this case, a silica plug is positioned in the capillary and is thereafter heated to produce a scintered plug. Moreover, besides polyacrylamide, other materials suitable for forming the gel stack of the present invention include agarose.

Samples for analysis are loaded into the end of the tube containing the gel. As described previously, depending on the material of the gel and the degree of its cross-linkage, the gel will effectively exclude macromolecules of a certain molecular weight range from analysis (in the highly cross-linked case) or it will effectively retard and pre-separate the macromolecules so as to provide a means for sequential analysis of small solutes before analysis of larger solutes. The actual analysis of the solutes occurs in the free zone portion of the modified capillary. It is contemplated that devices of the invention can be readily incorporated into conventional capillary electrophoresis systems currently in use. In this regard, a detector senses the passage of sample zones that migrate pass the detector.

It is to be understood that while the invention has been described above in conjunction with the preferred specific embodiments, the description and examples are intended to illustrate and not limit the scope of the invention, which is defined by the scope of the appended claims.

It is claimed:

1. An apparatus, useful for separating molecules by capillary electrophoresis, comprising:
    an elongated tube having a substantially cylindrical bore, said elongated tube defining a first portion and a second portion, wherein the first portion includes means for filtering molecules on the basis of molecular weight, the second portion of a construction sufficient to permit separations of molecules by electrical charge when flowed through the bore, the first and second portions in sequential fluid communication.

2. The apparatus as in claim 1 wherein the filtering means of the first portion substantially retards or prevents large macromolecules from flowing from the first portion into the second portion while permitting passage of other molecules into the second portion.

3. The apparatus as in claim 2 wherein the filtering means of the first portion includes a selectively permeable polymer substantially plugging an end of the bore adjacent to the first portion.

4. The apparatus as in claim 3 wherein the bore has a diameter not greater than about 200μ.

5. The apparatus as in claim 4 wherein the polymer substantially fills the first portion bore and is held therein.

6. The apparatus as in claim 3 wherein the polymer includes cross-linked polyacrylamide or agarose.

7. The apparatus as in clam 1 wherein the filtering means of the first portion includes a selectively permeable polymer substantially plugging an end of the bore adjacent to the first portion.

* * * * *